US00PP23213P2

(12) United States Plant Patent
Misato

(10) Patent No.: US PP23,213 P2
(45) Date of Patent: Nov. 27, 2012

(54) ***MANDEVILLA* PLANT NAMED 'SUNPARAROSTA'**

(50) Latin Name: *Mandevilla hybrida*
Varietal Denomination: Sunpararosta

(75) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 13/506,175

(22) Filed: Mar. 31, 2012

(51) Int. Cl.
*A01H 5/00* (2006.01)

(52) U.S. Cl. ..... Plt./232

(58) Field of Classification Search ..... Plt./232
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Mandevilla* plant named 'Sunpararosta', characterized by its compact and vining plant habit; vigorous growth habit; freely branching habit and short internodes, dense and bushy plant form; freely flowering habit; long flowering period; and medium-sized dark pink-colored flowers.

1 Drawing Sheet

Botanical designation: *Mandevilla hybrida.*
Cultivar denomination: 'SUNPARAROSTA'.

BACKGROUND OF THE INVENTION

The present invention relates to a new and distinct cultivar of *Mandevilla* plant, botanically known as *Mandevilla hybrida* and hereinafter referred to by the name 'Sunpararosta'.

The new *Mandevilla* plant is a product of a planned breeding program conducted by the Inventor in Higashiomi, Shiga, Japan. The objective of the breeding program is to create new freely-branching and vining *Mandevilla* plants with numerous pink-colored flowers.

The new *Mandevilla* plant originated from an open-pollination in Higashiomi, Shiga, Japan in April, 2006 of a proprietary selection of *Mandevilla hybrida* identified as code number M997, not patented, as the female, or seed parent with an unknown selection of *Mandevilla hybrida*, as the male, or pollen, parent. The new *Mandevilla* plant was discovered and selected by the Inventor as a single flowering plant from within the progeny of the stated open-pollination in a controlled greenhouse environment in Higashiomi, Shiga, Japan in October, 2007.

Asexual reproduction of the new *Mandevilla* plant by cuttings in Higashiomi, Shiga, Japan since October, 2007 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpararosta'. These characteristics in combination distinguish 'Sunpararosta' as a new and distinct *Mandevilla* plant:

1. Compact and vining plant habit.
2. Vigorous growth habit.
3. Freely branching habit and short internodes, dense and bushy plant form.
4. Freely flowering habit.
5. Long flowering period.
6. Medium-sized dark pink-colored flowers.

Plants of the new *Mandevilla* can be compared to plants of the female parent selection. Plants of the new *Mandevilla* differ primarily from plants of the female parent selection in flower color as plants of the female parent selection have rose pink-colored flowers.

Plants of the new *Mandevilla* can be compared to plants of the *Mandevilla* 'Sunmandecripi', disclosed in U.S. Plant Pat. No. 18,578. In side-by-side comparisons conducted in Higashiomi, Shiga, Japan, plants of the new *Mandevilla* differed from plants of 'Sunmandecripi' in the following characteristics:

1. Plants of the new *Mandevilla* had shorter lateral branches and shorter internodes than plants of 'Sunmandecripi'.
2. Plants of the new *Mandevilla* had smaller leaves than plants of 'Sunmandecripi'.
3. Plants of the new *Mandevilla* had smaller and shorter flowers than plants of 'Sunmandecripi'.
4. Plants of the new *Mandevilla* and 'Sunmandecripi' differed slightly in flower color.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpararosta' grown in a container.

The photograph at the bottom of the sheet is a close-up view of a typical flower of 'Sunpararosta'.

DETAILED BOTANICAL DESCRIPTION

The aforementioned photographs and following observations, measurements and values describe plants grown during the early autumn in 15-cm containers in an outdoor nursery in Higashiomi, Shiga, Japan and under commercial cultural practices. During the production of the plants, day temperatures averaged 25° C. and night temperatures averaged 15° C. Plants were five months old when the photographs and detailed description were taken. In the following description, color references are made to The Royal Horticultural Society Colour Chart, 2001 Edition, except where general terms of ordinary dictionary significance are used.

Botanical classification: *Mandevilla hybrida* 'Sunpararosta'.

Parentage:

*Female, or seed, parent*.—Proprietary selection of *Mandevilla hybrida* identified as code number M997, not patented.

*Male, or pollen, parent*.—Unknown selection of *Mandevilla hybrida*, not patented.

Propagation:

*Type*.—By vegetative cuttings.

*Time to initiate roots*.—About two weeks at 23° C. to 25° C.

*Time to produce a rooted young plant*.—About five to six weeks at 23° C. to 25° C.

*Root description*.—Fibrous; light brown in color.

*Rooting habit*.—Freely branching; medium density.

Plant description:

*Plant and growth habit*.—Compact and vining plant habit; vigorous growth habit; freely branching habit. Lateral branch description: Length: About 131.4 cm. Diameter: About 2.2 mm. Internode length: About 3 cm. Strength: Strong. Texture: Smooth, glabrous. Color, developing: Close to 144A. Color, mature: Close to N199B.

Foliage description:

*Arrangement*.—Opposite, simple.

*Length*.—About 5.8 cm.

*Width*.—About 4 cm.

*Shape*.—Elliptical.

*Apex*.—Cuspidate.

*Base*.—Obtuse.

*Margin*.—Entire.

*Texture, upper and lower surfaces*.—Smooth, glabrous.

*Venation pattern*.—Pinnate, reticulate.

*Color*.—Developing leaves, upper surface: Close to 146B. Developing leaves, lower surface: Close to 146C. Fully expanded leaves, upper surface: Close to 147A; venation, close to 143B. Fully expanded leaves, lower surface: Close to 147B; venation, close to 199D tinted with close to 177B.

*Petiole length*.—About 1.2 cm.

*Petiole diameter*.—About 1 mm.

*Petiole texture, upper and lower surfaces*.—Smooth, glabrous.

*Petiole color, upper and lower surfaces*.—Close to 143A tinted with close to 177B.

Flower description:

*Flower type and habit*.—Single salverform flowers arranged in axillary racemes; flowers face mostly outwardly; freely flowering habit with about four flowers per inflorescence.

*Natural flowering season*.—Plants begin flowering about six weeks after planting; long flowering period, plants flower continuously from early summer to late autumn in Japan.

*Flower longevity on the plant*.—About seven to ten days; flowers not persistent.

*Fragrance*.—None detected.

*Inflorescence height*.—About 17.2 cm.

*Inflorescence diameter*.—About 9.9 cm.

*Flowers*.—Appearance: Flared trumpet, corolla fused and five-parted; flowers roughly star-shaped. Diameter: About 5.8 cm. Depth (length): About 7.3 cm. Throat diameter: About 1.6 cm. Tube length: About 2.7 cm. Tube diameter, mid-section: About 1.4 cm. Tube diameter, base: About 4.6 mm.

*Flower buds*.—Height: About 6 cm. Diameter: About 1.1 cm. Shape: Lenticular. Color: Towards the apex, close to 63B; mid-section, close to 63D; towards the base, close to 47A and 145B.

*Corolla*.—Quantity and arrangement: Five petals arranged in a single whorl and fused at the base. Petal length: About 3.2 cm. Petal width: About 2.7 cm. Petal shape: Orbicular. Petal apex: Cuspidate. Petal margin: Entire; slightly undulate. Petal texture, upper and lower surfaces: Smooth, glabrous. Throat texture: Smooth, glabrous. Tube texture: Smooth, glabrous. Color: Petal, when opening, upper surface: Close to N66A. Petal, when opening, lower surface: Close to N66C. Petal, fully opened, upper surface: Close to 67C to 67D. Petal, fully opened, lower surface: Close to N66C. Throat: Towards the petal, close to 67A; towards the base, close to 7A. Tube: Close to N66C; towards the base, close to 145D.

*Calyx/sepals*.—Quantity and arrangement: Five sepals arranged in a single whorl. Sepal length: About 9.8 mm. Sepal width: About 2.4 mm. Sepal shape: Trullate. Sepal apex: Acuminate. Sepal base: Obtuse. Sepal margin: Entire. Sepal texture, upper and lower surfaces: Smooth, glabrous. Sepal color: When developing, upper and lower surfaces: Close to 144C; towards the apex, close to 61C. Fully developed, upper and lower surfaces: Close to 144C; towards the apex, close to 61C.

*Peduncles*.—Length: About 2.4 cm. Diameter: About 1.7 mm. Texture: Smooth, glabrous. Strength: Flexible, but strong. Color: Close to 143A.

*Pedicels*.—Length: About 2.1 cm. Diameter: About 1.8 mm. Texture: Smooth, glabrous. Strength: Flexible, but strong. Color: Close to 180B.

*Reproductive organs*.—Stamens: Quantity and arrangement: Typically five; filaments fused to corolla; anthers, connivent. Anther shape: Ellipsoidal. Anther size: About 0.8 mm by 9.2 mm. Anther color: Close to 4A. Pollen amount: Moderate. Pollen color: Close to 12C. Pistils: Quantity: Typically one. Pistil length: About 2.4 cm. Style color: Close to 144D. Stigma shape: Conical. Stigma color: Close to 144D. Ovary color: Close to 144B.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpararosta' as illustrated and described.

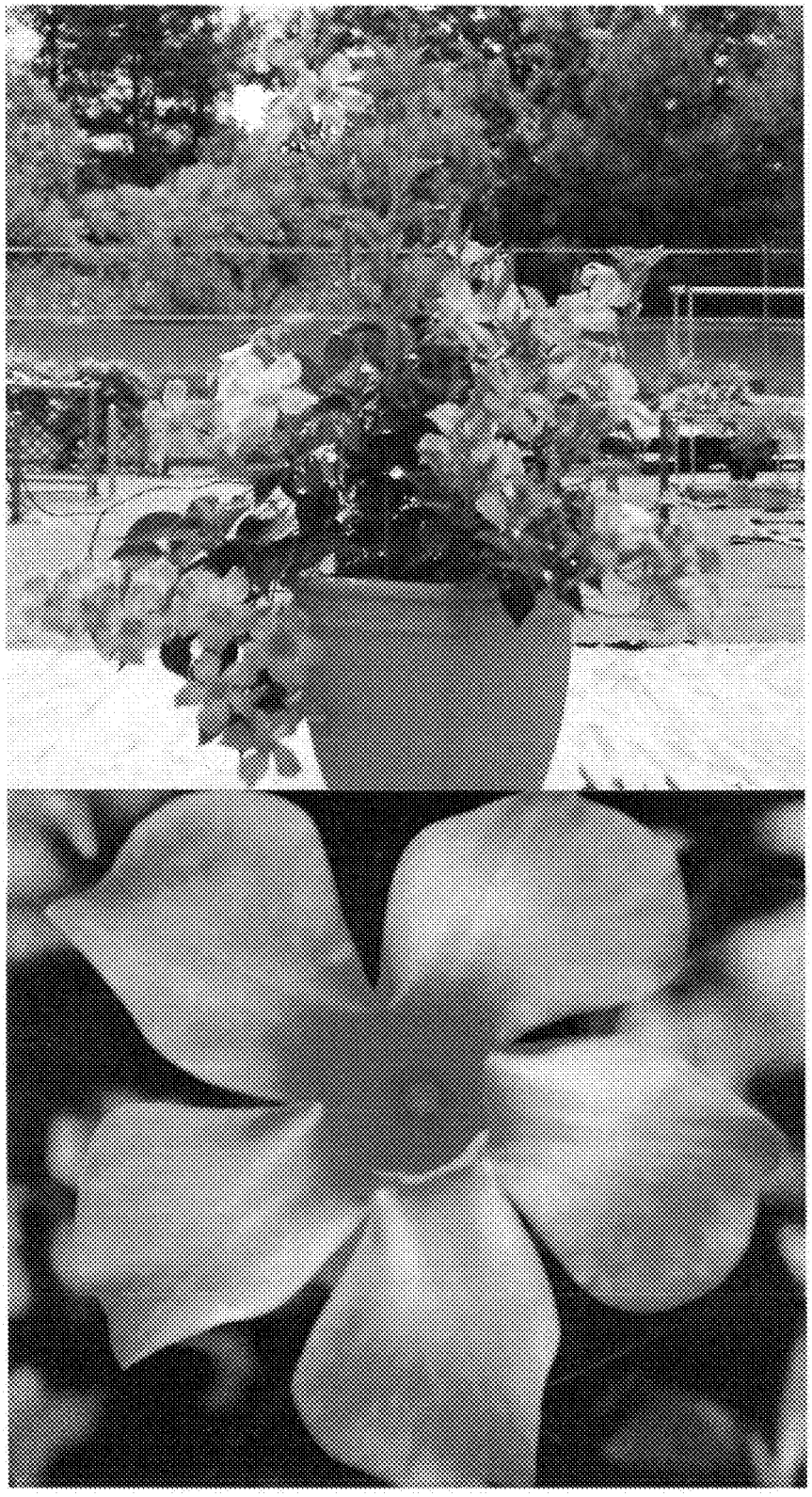

* * * * *